US008568966B2

(12) United States Patent
Arinaga et al.

(10) Patent No.: US 8,568,966 B2
(45) Date of Patent: Oct. 29, 2013

(54) METHOD AND APPARATUS FOR PRODUCING A MOLECULAR FILM WITH AN ADJUSTED DENSITY

(75) Inventors: Kenji Arinaga, Kawasaki (JP); Ulrich Rant, Munich (DE); Erika Pringsheim, Munich (DE); Jelena Knezevic, Munich (DE)

(73) Assignee: Fujitsu Limited, Kawasaki (JP)

( * ) Notice: Subject to any disclaimer, the term of this patent is extended or adjusted under 35 U.S.C. 154(b) by 1795 days.

(21) Appl. No.: 11/700,264

(22) Filed: Jan. 31, 2007

(65) Prior Publication Data

US 2008/0003666 A1 Jan. 3, 2008

(30) Foreign Application Priority Data

Jan. 31, 2006 (JP) ................................. 2006-023715

(51) Int. Cl.
  *C12Q 1/00* (2006.01)
(52) U.S. Cl.
  USPC ................................ 435/4; 436/524; 436/525
(58) Field of Classification Search
  None
  See application file for complete search history.

(56) References Cited

U.S. PATENT DOCUMENTS

| 5,635,047 | A | 6/1997 | Porter et al. ................... 204/421 |
| 6,329,209 | B1 * | 12/2001 | Wagner et al. ................... 506/13 |
| 6,514,762 | B1 | 2/2003 | Wang ............................ 435/461 |
| 2002/0192722 | A1 * | 12/2002 | Stolowitz et al. ............... 435/7.9 |
| 2005/0069932 | A1 | 3/2005 | Arinaga et al. |
| 2006/0040378 | A1 | 2/2006 | Arinaga et al. |

FOREIGN PATENT DOCUMENTS

| JP | 2006-058094 | 3/2006 |
| WO | 02/055993 | 7/2002 |
| WO | WO 2004/005582 A2 | 1/2004 |

OTHER PUBLICATIONS

T. G. Drummond et al.; "Electrochemical DNA sensors;" *Nature Biotechnology*; vol. 21; No. 10; pp. 1192-1199. (2003).
J. Wang; "Survey and Summary From DNA biosensors to gene chips;" *Nucleic Acids Research*; vol. 28; No. 16; pp. 3011-3016. (2000).
U. Rant et al.; "Dynamic Electrical Switching of DNA Layers on a Metal Surface;" *NANO Letters*; vol. 4; No. 12; pp. 2441-2445. (2004).
R. J. Heaton et al.; "Electrostatic surface plasmon resonance: Direct electric field-induced hybridization and denaturation in monolayer nucleic acid films and label-free discrimination of base mismatches;" *PNAS*; vol. 98; No. 7; pp. 3701-3704. (2001).
A. W. Peterson et al.; "The effect of surface probe density on DNA hybridization;" *Nucleic Acids Research*; vol. 29; No. 24; pp. 5163-5168. (2001).

(Continued)

*Primary Examiner* — Chris L Chin
(74) *Attorney, Agent, or Firm* — Kratz, Quintos & Hanson, LLP

(57) ABSTRACT

An object of the present invention is to provide a technique that can adjust a molecular density of the film of functional molecules (e.g. DNA molecules), which is utilized for biochips such as DNA chip, to a desired degree efficiently and easily. The method for producing a molecular film with an adjusted density according to the present invention includes forming a molecular film and adjusting a molecular density. In the forming a molecular film, a molecular film composed of molecules is formed on a conductive substrate, wherein the molecule includes a region capable of binding to the conductive substrate at least in a portion thereof. In the density adjusting, a molecular density of the molecular film is adjusted by desorbing a part of the molecules which make up the molecular film from the conductive substrate.

10 Claims, 4 Drawing Sheets

(56) References Cited

OTHER PUBLICATIONS

C. Zhong et al.; "Fine structure in the voltammetric desorption curves of alkanethiolate monolayers chemisorbed at gold;" *Journal of Electroanalytical Chemistry*; pp. 147-153. (1997), vol. 425.

D. F. Yang et al.; "Studies of the Electrochemical Removal and Efficient Re-formation of a Monolayer of Hexadecanethiol Self-Assembled at an Au(111) Single Crystal in Aqueous Solutions;" *Langmuir*; vol. 13; pp. 243-249. (1997).

A. Ulman; "Formation and Structure of Self-assembled Monolayers;" *Chemical Reviews*; vol. 96; No. 4, pp. 1533-1554. (1996).

R. Georgiadis et al.; "Quantitative Measurements and Modeling of Kinetics in Nucleic Acid Monolayer Films Using SPR Spectroscopy;" *Journal of American Chemical Society*; vol. 122; pp. 3166-3173. (2000).

A. B. Steel et al.; "Electrochemical Quantitation of DNA Immobilized on Gold;" *Analytical Chemistry*; vol. 70; No. 22; pp. 4670-4677. (1998).

K. A. Peterlinz et al.; "In Situ Kinetics of Self-Assembly by Surface Plasmon Resonance Spectroscopy;" *Langmuir*; vol. 12; pp. 4731-4740. (1996).

T. M. Herne et al.; "Characterization of DNA Probes Immobilized on Gold Surfaces;" *Journal of American Chemical Society*; vol. 119, No. 38; pp. 8916-8920. (1997).

German Office Action dated Jul. 4, 2007, DE102007005472.8-41.

* cited by examiner

METHOD AND APPARATUS FOR PRODUCING A MOLECULAR FILM WITH AN ADJUSTED DENSITY

CROSS-REFERENCE TO RELATED APPLICATIONS

This application is based upon and claims the benefits of the priority from the prior Japanese Patent Application No. 2006-023715, filed on Jan. 31, 2006, the entire contents of which are incorporated herein by reference.

BACKGROUND OF THE INVENTION

1. Field of the Invention

The present invention relates to a method and apparatus for producing a molecular film with an adjusted density that are utilized for biochips such as DNA chip.

2. Description of the Related Art

Nanotechnology has recently become a key word which has drawn much attention from many people, partly because of the influence of a nanotechnology initiative proposed in the United States in 2,000.

In the nanotechnology, nanobiotechnology, an interdisciplinary area between semiconductor microprocessing technology (semiconductor nanotechnology) and biotechnology, is a new field that may bring about drastic solutions to the conventional problems, and research and development have been carried out actively in this field.

In the nanobiotechnology, biochips represented by DNA chips (or DNA microarrays) attract attention as an effective means in the field such as clinical diagnosis and drug therapy. The biochip comprises a substrate made of glasses, silicon, plastics, metal etc, on which a large number of different test substances of biomacromolecules such as DNA and protein are spotted and arrayed at a high density. Such biochips can simplify examination of nucleic acids and proteins and are particularly effective for gene analysis. (See, 'Electrochemical DNA sensors' T. G. Drummond et al, Nature Biotech., 2003, Vol. 21, No. 10, 1192-1199, and 'SURVEY AND SUMMARY Prom DNA biosensors to gene clips' J. Wang, Nucleic Acids Research, 2000, Vol. 28, No. 16, 3011-3016).

Also, in recent years, attention has been paid to devices, called "MEMS" or "µTAS", for greatly improving the detection sensitivity and detection time compared with the conventional devices. Such devices are manufactured by attaching molecules bound with functional molecules to a solid substrate to form a functional surface (detecting element) partially, where micromachining technology and microsensing technology are integrated and techniques to detect minute analytes are used. The term "MEMS" is the abbreviation of Micro Electro Mechanical Systems, that is, a technology to prepare microscopic matters, based on semiconductor processing technology, or microscopic, precision devices prepared using the technology. In general, it is a system wherein a plurality of functional components such as mechanical, optical and hydrodynamic components are integrated and miniturized. The term "µTAS" is an abbreviation of Micro Total Analysis System and is a chemical analysis system in which micropumps, microvalves, sensors etc. are miniaturized, accumulated, and integrated in general, these devices have a functional surface in which functional molecules that have a specific function, or molecules bound with the functional molecules are immobilized or bound on a substrate via a sulfur atom in a self-assembled manner. In these devises, reaction at the functional surface is evaluated electrically or optically, mid in addition, it is possible to promote the reaction at the functional surface or amplify the signal resulting from the reaction by applying an external electrical signal using the substrate on which molecules are immobilized as an electrode (See, 'Dynamic Electrical Switching of DNA Layers on a Metal Surface' U. Rant et al., Nano Lett., 2004, Vol 4, No. 12, 2441-2445, and 'Electrostatic surface plasmon resonance: Direct electric field-induced hybridization and denaturation in monolayer nucleic acid films and label-free discrimination of base mismatches' R. J. Heaton et al., Proc. Natl. Acad. Sci. USA, 2001, Vol. 98, No. 7, 3701-3704).

In such devises, immobilization of the functional molecules on a substrate (electrode) is an important elemental technology. Of such technology, a technique for forming a self assembled monolayer (SAM), in which a self assembled monolayer is formed on the substrate (electrode) via a sulfur atom, has many advantages because the technique enables the functional molecules to be immobilized or bound on the substrate (electrode) at low cost and with ease. Therefore, the technique is especially effective for forming a dense monolayer.

However, when the functional molecules are immobilized or bound on the substrate (electrode) as a dense monolayer, there is a problem as follows. Specifically, when, for example, a bond between the functional molecule and a target molecule is observed or when the immobilized or bound functional molecule is bound to a larger target molecule, steric hindrance between adjacent functional molecules causes a major problem.

For example, in the case of DNA chip in which a target DNA serves as the target molecule and a complementary DNA to the target DNA serves as the functional molecule, hybridization efficiencies drop depending on the increase of the density of immobilized or bound complementary DNA (See, 'The effect of surface probe density on DNA hybridization' A. W. Peterson et al., Nucleic Acids Research, 2001, Vol. 29, No. 24, 5163-5168). With the increase of the density of immobilized or bound functional molecule (complementary DNA), steric hindrance between the functional molecules (complementary DNAs) increases, resulting in the decrease of space required for hybridization and causing such phenomenon, the decrease of hybridization efficiency. Therefore, in the DNA chip, it is necessary to control the density of the complementary DNA (functional molecule), as a probe, immobilized or bound on a substrate (electrode) to a desired degree.

Previously, the density of the functional molecule immobilized or bound on a substrate (electrode) is controlled, for example, by the following known methods: (1) a method using time as an indicator in which the density is controlled by considering diffusion time of the functional molecules on the substrate (electrode); and (2) a method used when the functional molecule is a charged molecule, in which the density is controlled utilizing the screening effect of counterion (Debye screening effect). By these methods, the self assembled monolayer was formed as a film in which functional molecules are dispersed to some extent.

In order to make the density of the immobilized or bound functional molecule relatively low, however, both methods must be performed under very strict condition since in the case of the method of (1), diffusion of the functional molecules is proportional to the square root of the time, and in the case of the method of (2), the screening effect is proportional to the square root of the concentration of the counterion (See, 'In Situ Kinetics of Self-Assembly by Surface Plasmon Resonance Spectroscopy' K. A. Peterlinz et al., Langmuir, 1996, Vol. 12, No. 20, 4731-4740, and 'Characterization of DNA Probes Immobilized on Gold Surfaces' T. M. Herne et al., J. Am. Chem. Soc., 1997 Vol. 119, No. 38, 8916-8920, and 'Effective Size Determining Method of Molecule, Method for Bonding Molecule to Substrate, and Molecule Detection Device' Japan patent application 2006-58094).

Thus, currently, the development of technique has been desired that can adjust the density of the film of functional molecules (e.g. DNA molecules), which is utilized for biochips such as DNA chip, to a desired degree efficiently and easily.

In view of the above-mentioned current situation, the present invention has been done, and an object of the present invention is to solve conventional problems and to achieve the following objects. Specifically, an object of the invention is to provide a technique that can adjust the molecular density of the film of functional molecules (e.g. DNA molecules), which is utilized for biochips such as DNA chip, to a desired degree efficiently and easily, in other words, to provide a method and apparatus for producing a molecular film with an adjusted density that is suitable for biochips such as DNA chip.

SUMMARY OF THE INVENTION

The method for producing a molecular film with an adjusted density includes forming a molecular film composed of molecules on a conductive substrate, wherein the molecule includes a region capable of binding to the conductive substrate at least in a portion thereof, and adjusting a molecular density of the molecular film by desorbing a part of the molecules which make up the molecular film from the conductive substrate.

In the method for producing a molecular film with an adjusted density according to the invention, in the forming a molecular film, a molecular film composed of molecules is formed on a conductive substrate, wherein the molecule includes a region capable of binding to the conductive substrate at least in a portion thereof. In the density adjusting, a molecular density of the molecular film is adjusted by desorbing a part of the molecules which make up the molecular film from the conductive substrate. The molecular film produced in this way has a reduced molecular density that is adjusted to a desired range compared to the molecular film formed in the forming a molecular film due to the desorption of molecules from the molecular film. Consequently, when this molecular film is used for a variety of measurements, analyses, etc., the motion and function of individual molecules of the molecular film are exhibited sufficiently, and the reproducibility and quantitative ability of the molecular film can be improved remarkably, enabling measurement, analysis, etc. with high accuracy to be repeated stably.

The apparatus for producing a molecular film with an adjusted density includes a density adjusting unit configured to desorb a part of molecules which make up a molecular film from a conductive substrate to thereby adjust a molecular density of the molecular film, wherein the molecular film is formed on the conductive substrate (and the molecule includes a region capable of binding to the conductive substrate at least in a portion thereof.

In the apparatus for producing a molecular film with an adjusted density according to the invention, the density adjusting unit desorbs a part of molecules which make up a molecular film from a conductive substrate to thereby adjust a molecular density of the molecular film, wherein the molecular film is formed on the conductive substrate and the molecule includes a region capable of binding to the conductive substrate at least in a portion thereof. The molecular film produced in this way has a reduced molecular density that is adjusted to a desired range compared to the molecular film before the adjustment of the molecular density by the density adjusting unit due to the desorption of molecules from the molecular film. Consequently, when this molecular film is used for a variety of measurements, analyses, etc., the motion and function of individual molecules of the molecular film are exhibited sufficiently, and the reproducibility and quantitative ability of the molecular film can be improved remarkably, enabling measurement, analysis, etc. with high accuracy to be repeated stably.

Figure 1:
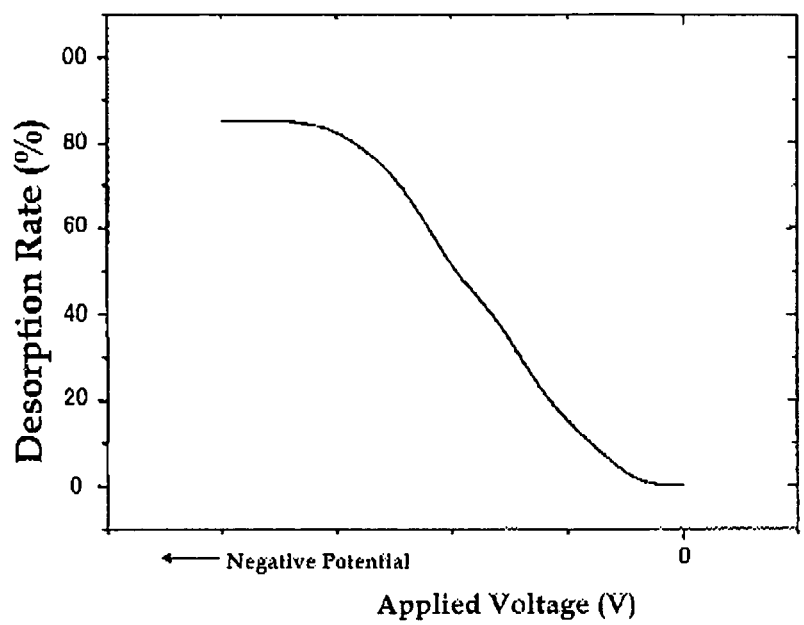
FIG. 1 is a graph showing a relation between the electrical potential (V) applied to a conductive substrate or electrode layer (electrode), and the desorption rate (%) of the molecule desorbed from the conductive substrate or electrode layer.

DESCRIPTION OF THE PREFERRED EMBODIMENTS (Method and Apparatus for Producing a Molecular Film with an Adjusted Density)

The method for producing a molecular film with an adjusted density according to the invention comprises a molecular film forming step and a density adjusting step, and may further comprise other steps appropriately selected on an as-needed basis.

The apparatus for producing a molecular film with an adjusted density according to the invention comprises a density adjusting unit, and may further comprise other units appropriately selected on an as-needed basis, for example, a molecular film forming unit.

The method for producing a molecular film with an adjusted density according to the invention can be suitably carried out employing the apparatus for producing a molecular film with an adjusted density according to the invention. While explaining the method for producing a molecular film with an adjusted density according to the invention blow, the apparatus for producing a molecular film with an adjusted density according to the invention will also be described in detail through the explanation.

—Molecular Film Forming Step and Molecular Film Forming Unit—

The molecular film forming step is a step in which a molecular film composed of molecules is formed on a conductive substrate, wherein the molecule comprises a region capable of binding to the conductive substrate at least in a portion thereof. The molecular film forming step can be suitably carried out by the molecular film forming unit of the apparatus for producing a molecular film with an adjusted density according to the invention.

The molecular film forming unit is a unit configured to form a molecular film composed of molecules on a conductive substrate, wherein the molecule comprises a region capable of binding to the conductive substrate at least in a portion thereof.

—Conductive Substrate—

The conductive substrate is not particularly limited and can be appropriately selected depending on the application. The structure thereof may be a single-layer structure or may be a multilayer structure, for example. The conductive substrate may be formed of a conductive material in whole, or the conductive substrate may be constructed such that an electrode layer made of a conductive material is provided on an insulating substrate.

The shape, structure, size, surface character, number, and the like of the conductive substrate, insulating substrate, or electrode layer are not particularly limited and can be appropriately selected depending on the application. Examples of the shape include a flat plate shape, circle shape, and ellipse shape. The size is not particularly limited and can be appropriately determined depending on the application. Examples of the surface character include a gloss surface and rough surface. These may be used alone or in combination.

Examples of suitable material for the insulating substrate include quartz glass, silicon, silicon oxide, silicon nitride, and sapphire. These may be used alone or in combination.

The material for the conductive material or electrode layer is not particularly limited as long as it is conductive; examples thereof include metals, alloys, conductive resins, and carbon compounds. Examples of the metal include gold, platinum, silver, copper, and zinc. Examples of the alloy include alloys of two or more different metals exemplified as the metal above. Examples of the conductive resin include polyacetylene, polythiophene, polypyrrole, polyphenylene, polyphenylene vinylene, and polyaniline. Examples of the carbon compound include conductive carbon and conductive diamond. These may be used alone or in combination.

When the electrode layer is provided on the insulating substrate, in order to improve adhesiveness between the electrode layer and the insulating substrate, an adhesive layer may be formed therebetween.

The material, shape, structure, thickness, size, and the like of the adhesive layer are not particularly limited and can be appropriately selected depending on the application. Examples of the material include chromium and titanium. The structure is not particularly limited and can be appropriately selected depending on the application. It may be a single-layer structure or may be a multilayer structure.

The size, shape, and the like of the electrode layer may be appropriately adjusted, to a desired degree by coating the surface with an insulating film to make only a part of the electrode layer exposed. The number of the electrode layer is not particularly limited and can be appropriately selected depending on the application. It may be one or may be two or more.

The material, shape, structure, thickness, size, and the like of the insulating film are not particularly limited and can be appropriately selected from those known in the art depending on the application. Examples of suitable material include amorphous glass, oxides or nitrides such as non-doped or doped $SiO_2$ or $SiN_x$ and high molecular compounds such as polyimide and photoresist. Examples of the photoresist material include g-line resists, i-line resists, KrF resists, ArF resists, F2 resists, and electron beam resists.

In the invention, in order to apply an electrical potential to the conductive substrate or electrode layer (work electrode), a counter electrode, reference electrode, or the like, which are different from those work electrodes, is preferably provided. Such electrode may be one or may be two or more, The counter electrode is arranged facing the conductive substrate or electrode (work electrode) and is an, electrode for applying a electrical potential to these. The reference electrode is an electrode for adjusting the electrical potential between the conductive substrate or electrode layer (work electrode). Adjustment of electrical potential using the reference electrode is known as a three-electrode method.

When two or more of the conductive substrate or electrode layer (work electrode) are provided, applying or varying the electrical potential to the conductive substrate or electrode layer (work electrode) arbitrarily and at different timing makes it possible to desorb the molecules immobilized or bound on each work electrode layer at different timing.

—Molecule—

The molecule is not particularly limited as long as it comprises a region capable of binding to the conductive substrate or electrode layer at least in a part thereof and can be appropriately selected depending on the application.

The binding to the conductive substrate or electrode layer is not particularly limited and can be appropriately selected depending on the application; examples thereof include electrical bond, chemical bond, and adsorption. The chemical bond is preferable since the desorption of some of the molecules, which make up a molecular film, from the molecular film formed of the molecules in the density adjusting step can be controlled easily. Among the chemical bonds, sulfur atom (S)-containing bonds are preferable in terms of control of cleavage, etc., and specifically, binding of molecule that comprises a thiol bond (—SH), disulfide bond (—S—S—), or the like, and the conductive substrate or electrode layer is most preferable. When a molecule that comprises the thiol bond (—SH) or disulfide bond (—S—S—) is bound to the conductive substrate or electrode layer, the application of a specific electrical potential to the conductive substrate or electrode layer leads to the cleavage of the bond between the sulfur atom (S) and the conductive substrate or electrode layer, causing the desorption of some of the molecules, which make up the molecular film, from the conductive substrate or electrode layer. As a result, when the molecular film is a dense film of the molecules, the molecular density of the molecular film is reduced by the desorption of some of the molecules and adjusted to a desired degree.

The molecule may be any shape without limitation and the shape can be appropriately selected depending on the application; examples thereof include linear, granular, plate-like, and combination of two or more of these. Among these, linear or the like is preferable.

The molecule may be ally molecule without limitation and can be appropriately selected depending on the application. For example, in terms of application to the treatment, diagnosis, etc, of disease, biomolecules and the like are suitable. In either case where the molecule is a biomolecule or other molecule, in the density adjusting step, some of the molecules, which make up the molecular film, are desorbed to adjust the molecular density of the molecular film to a desired degree. When the resulting molecular film is used as a sensor, etc., it is preferable that the behavior of the molecules, which make up the molecular film, can, be controlled electrically. In order to achieve such molecular film, the molecules, which make up the molecular film are preferably capable of interacting with the conductive substrate electrically. Suitable examples of such molecule include charged molecules. Examples of the charged molecule include ionic polymers. Examples of the ionic polymer include cationic polymers and anionic polymers. Examples of suitable cationic polymer (positively charged ionic polymer) include guanidine DNAs and polyamines. Examples of suitable anionic polymer (negatively charged ionic polymer) include polynucleotides and polyphosphoric acids. These are preferable in that the interaction (e.g. binding) with the conductive substrate or electrode layer can be controlled easily because negative charge is present in the molecule at a specific interval. These molecules may be used alone or in combination.

In the invention, polynucleotides that comprise the thiol bond (—SH) or disulfide bond (—S—S—) in a portion of the molecule thereof are preferable, and DNAs RNAs, and complexes of these and proteins, which comprise the thiol bond (—SH) or disulfide bond (—S—S—) at their ends, respectively, are most preferable. The DNA and RNA may be single-stranded or may be double-stranded.

The size or length of the molecule is not particularly limited and can be appropriately determined depending on the application. When the molecule is the polynucleotide, it preferably consists of at least 6 bases.

The molecule preferably comprises a target capture portion that is capable of capturing a target in terms of utilization of the molecular film formed of the molecules to diagnosis, analysis, etc. Specific examples of the target capture portion include antibodies, antigens, enzymes, and coenzymes for the target. The number of the target capture portion per molecule of the capturing agent is not particularly limited and can be appropriately selected depending on the application. The number thereof may be one or two or more. The position of the target capture portion in the capturing agent is not particularly limited and can be appropriately selected depending on the application. When the interaction portion is linear, the position is, for example, its end or the like. When the interaction portion is a polynucleotide, the position may be 3' end or may be 5' end.

The target is not particularly limited and can be appropriately selected depending on the application; examples thereof include organic molecules. Examples of the organic molecule include proteins, plasma proteins, tumor markers, apoproteins, viruses, autoantibodies, clotting or fibrinolytic factors, hormones, drugs in the blood, nucleic acids, HLA antigens, lipoproteins, glycoproteins, polypeptides, lipids, poly-saccharides, and lipopolysaccharides.

In addition, the molecule preferably comprises a light-emitting portion that is capable of emitting light upon irradiation with light when the molecule is desorbed from the conductive substrate or electrode layer, or that is capable of emitting light upon inadiation with light while the molecule is immobilized or bound on the conductive substrate or electrode layer. This is advantageous in that diagnosis, etc. can be performed with eyes or optical detectors. Examples of the optical detector include photo multipliers, photo diodes, photo transistors and fluorescence microscopes.

The number of the light-emitting portion per one molecule is not particularly limited and can be appropriately selected depending on the application; it is at least one and may be two or more. The position of the light-emitting portion in the molecule is not particularly limited and can be appropriately selected depending on the application. When the region capable of interacting is linear, the position is, for example, its end or the like. When the region capable of interacting is a polynucleotide; the position may be 3' end or may be 5' end.

The light-emitting portion is not particularly limited and can be appropriately selected depending on the application; suitable examples thereof include fluorescent dyes, metals, and semiconductor nanospheres.

When the electrode for adsorption and desorption is made of metal, like metal electrode, fluorescent dyes that can be most suitably used as the light-emitting portion are such that they do not emit light during interaction with the metal (for example, while the molecule is located close to the metal) even if irradiated with light having a wavelength at which the fluorescent dye is capable of absorbing light, but when there is no interaction with the metal (for example, when the molecule stays away from the metal), upon irradiation with light having a wavelength at which the fluorescent dye is capable of absorbing light, they can emit light using the light energy. The fluorescent dye is not particularly limited and can be appropriately selected from those known in the art depending on the application. Examples of suitable fluorescent dye include compounds expressed by the following Structural Formula 1.

Structural Formula 1

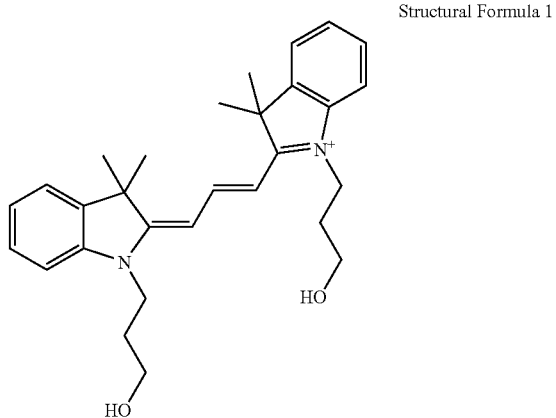 [SMILES: CC1(C)C(/C=C/C=C2/N(CCCO)c3ccccc3C2(C)C)=[N+](CCCO)c2ccccc21]

The method for synthesizing the molecule is not particularly limited and can be appropriately selected depending on the application. For example, the molecule can be synthesized by any method such as a chemical synthesis method and fermentative production method. The molecule may be either a synthesized one or a commercially available one, For the molecule that is contained in the molecular film to be formed using the molecule, only one kind of molecule may be used, or two or more kinds of molecules may be used. When two or more kinds of molecules are used, different kinds of molecules may be present randomly in a dispersed manner, or may be present in a separate region.

—Molecular Film—

The molecular film is formed of the molecules and may be a monolayer or may be a multilayer of the monolayers. In the invention, the molecular film is preferably a monolayer in order for the molecular film to perform its function easily, and for the purpose of easy control of its function, The molecular film can be formed on the conductive substrate or electrode layer by any method without limitation and the method can be appropriately selected depending on the application. Examples thereof include Langmuir Blodgett technique (LB technique), Spin coating method, and dip method. Among them, the methods described in "Formation and Structure of Self-Assembled Monolayers' A. Ulman, Chem. Rev., 1996, Vol. 96, No. 4, 1533-1554" are most preferable. When the molecular film is formed by these forming methods, the molecules are preferably dispersed or dissolved in a liquid. In this case, the liquid is not particularly limited and can be appropriately selected depending on the application. Examples thereof include liquids that contain water, alcohol, or surfactant. In the molecular film formed on the conductive substrate or electrode layer by means of these forming methods, a portion of the molecule is bound to the conductive substrate or electrode layer through a chemical bond and the molecule is immobilized on the conductive substrate or electrode layer. When the molecule comprises the thiol bond (—SH) or disulfide bond (—S—S—), a bond is formed easily between the site of the thiol bond (—SH) or disulfide bond (—S—S—) and the conductive substrate or electrode layer. In this case, the molecules which make up the molecular film are immobilized on the conductive substrate or electrode layer via the sulfur atom (S) of the thiol bond (—SH) or disulfide bond (—S—S—), present in the molecule, by a chemical bond. Thus, the molecular film formed in the molecular film forming step is typically a self assembled monolayer (SAM) of the molecules and is densely packed.

When the molecular film is the dense film; however, the use of the molecular film for analysis, diagnosis, etc. reduces, for example, motility of each molecule making flip the molecular film, causing problems such as reduction of sensitivity.

Therefore, in the invention, the molecular film formed in the molecular film forming step is subjected to the density adjusting step below, by which the molecules which make up the molecular film are desorbed from the molecular film to adjust the molecular density of the molecular film to a desired degree.

—Density Adjusting Step and Density Adjusting Unit—

The density adjusting step is a step in which a part of the molecules which make up the molecular film is desorbed from the conductive substrate or electrode layer to thereby adjust a molecular density of the molecular film. The density adjusting step can be suitably carried out by the density adjusting unit of the apparatus for producing a molecular film with an adjusted density according to the invention.

The density adjusting unit is a unit configured to desorb a part of the molecules which make up a molecular film from a conductive substrate to thereby adjust a molecular density of the molecular film, wherein the molecular film is formed on the conductive substrate or electrode layer and the molecule comprises a region capable of binding to the conductive substrate or electrode layer at least in a portion thereof.

The molecular density of the molecular film can be suitably adjusted by applying an electrical potential to the conductive substrate or the electrode layer. When the molecule making up the molecular film comprises, for example, the bond between a sulfur atom (S) and the conductive substrate or electrode layer in a portion thereof, the application of an electrical potential to the conductive substrate or the electrode layer results in, the cleavage of the binding site, causing the desorption of the molecules from the conductive substrate or electrode layer. The bond between the sulfur atom (S) and conductive substrate or electrode layer is an oxidative bond and application of a specific reduction potential can result in the reductive desorption of the bond (See, 'Fine structure in the voltammetric desorption curves of alkanethiolate monolayers chemisorbed at gold' C. J. Zhong et al., J. Electroanal, Chem., 1997, Vol. 425, 147-153., and 'Studies of the Electrochemical Removal and Efficient Reformation of a Monolayer of Hexadecanethiol Self-Assembled at an Au(111) Single Crystal in Aqueous Solutions' D. Fe Yang et al., Langmuir, 1997, Vol. 13, No. 2, 243-249.). As a result, the molecular density of the molecular film is reduced, the steric hindrance between the molecules in the molecular film is diminished, and the motility of each molecule is improved. Thus, when the molecular film is employed for analysis, diagnosis, etc., the sensitivity of analysis, measurement, etc. is improved, for example.

The electrical potential to be applied to the conductive substrate or electrode layer is not particularly limited and can be appropriately selected depending on the material, shape, size, and number of the conductive substrate or electrode layer, the type of the molecule, the type of the binding of the molecule to the conductive substrate or electrode layer, the size of the molecule, and the like. If the electrical potential is not proper, the amount of molecule desorbed from the conductive substrate or electrode layer is not sufficient, by which the molecular density of the molecular film may not be reduced to a desired degree; or the molecular density of the molecular films may become too low, inviting the reduction of the sensitivity of analysis, measurement, etc. when the molecular film is used for analysis, measurement, etc.

In the density adjusting step, the electrical potential to be applied to the conductive substrate or electrode layer can be suitably controlled based on the indicator appropriately selected depending on the application.

Such indicator is not particularly limited and can be appropriately selected depending on the application; for example, (1) previously prepared relation diagram between desorption rate (%) and applied voltage (V), where the desorption rate (%) means an amount of the molecule desorbed from the conductive substrate or electrode layer per unit time during the application of an electrical potential, and (2) a signal that is directly related to the molecular density on the conductive substrate or electrode layer, are most suitable.

When the indicator of (1) mentioned above is used, the density adjusting step can be performed as follows. Specifically, an electrical potential is applied to the conductive substrate or electrode layer while adjusting the magnitude of electrical potential applied to the conductive substrate or electrode layer, and applied time based on the relation diagram, by which the molecules are desorbed from the conductive substrate or electrode layer to reduce the molecular density (molecules/cm$^2$) of the molecular film.

When the indicator of (2) mentioned above is used, the density adjusting step can be performed as follows. Specifically, while monitoring the molecular density (molecules/cm$^2$) of the molecule on the conductive substrate or electrode layer in real time, or while monitoring a signal directly related to the molecular density of the molecule on the conductive substrate or electrode layer in real time, an electrical potential is applied to the conductive substrate or electrode layer to desorb the molecules and to thereby reduce the molecular density (molecules/cm$^2$) of the molecular film. The signal is not particularly limited and can be appropriately selected depending on the application. For example, when the molecule comprises the fluorescent dye in a molecule thereof, fluorescence intensity (arbitrary unit: a.u.) generated by the fluorescent dye, and the like are suitable.

In this specification, the unit of the molecular density "molecules/cm$^2$" may be described as "cm$^{-2}$".

The density adjusting step reduces (adjusts) the molecular density of the molecular film, aid the resulting molecular density is different depending on the application of the molecular film, the type and size of the molecule making up the molecular film, and the like If the molecular density is not reduced to an appropriate degree compared to that of a dense film, the sensitivity or the like of analysis, measurement, etc. may not be satisfactory when the molecular film is used for a variety of analyses or measurements.

The desorption rate (%) of the molecule of the molecular film in the density adjusting step is not particularly limited and varies depending on the type, etc. of the molecule.

The electrical potential to be applied to the conductive substrate or electrode layer in the density adjusting step is not particularly limited and can be appropriately selected depending on the type, etc. of the molecule. For example, the electrical potential may be oxidation potential (positive electrical potential) or may be reduction potential (negative electrical potential). When the molecule is bonded to the conductive substrate or electrode layer through the bond between a sulfur atom (S) and the conductive substrate or electrode layer; reduction potential can be suitably adopted as the electrical potential.

As described above, in the density adjusting step, the electrical potential to be applied to the conductive substrate or electrode layer can be suitably controlled based on the indicator of (1) or (2) mentioned above. Hereinafter, specific examples of the control of the electrical potential to be applied to the conductive substrate or electrode layer will be described.

When the electrical potential is controlled based on the indicator of (1) mentioned above, desorption rate percentage of desorbed amount with respect to period of applied electrical potential) at a specific electrical potential is measured previously to obtain a relation diagram between electrical potential and desorbed amount (FIG. 1). Then, a specific electrical potential is applied to the conductive substrate or electrode layer and the electrical potential and the time are adjusted based on the relation diagram, which makes it possible to control the amount of desorbed molecule immobilized or bound on the conductive substrate or electrode layer to a desired degree.

Figure 2:
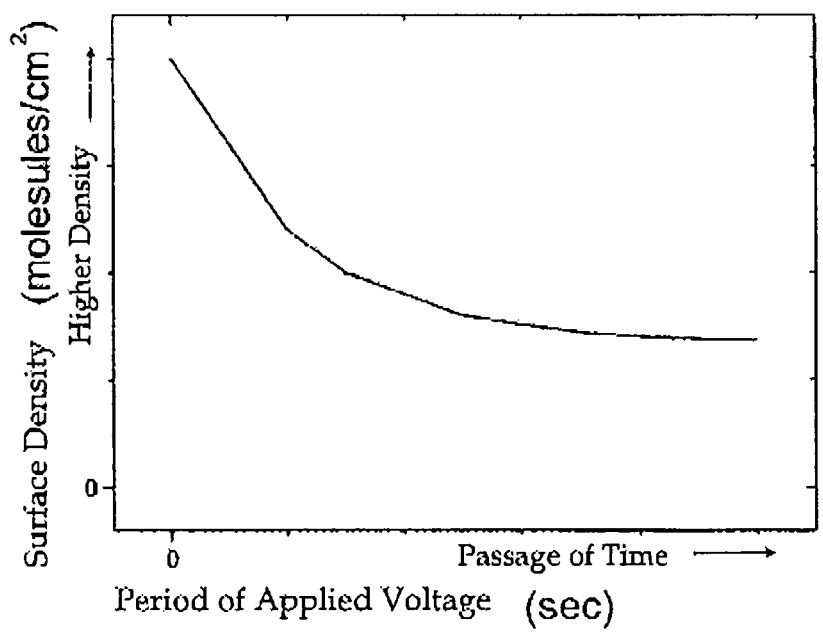
FIG. 2 is a graph showing a real-time change in molecular density (molecules/cm$^2$) of the molecules on the conductive substrate or electrode layer when a specific desorption potential is applied.

When the electrical potential is controlled based on the indicator of (2) mentioned above, while monitoring the attached amount (or molecular density) of the molecule immobilized or bound on the conductive substrate or electrode layer, a specific electrical potential is applied (for example, reduction potential is applied when the molecule is bonded to the conductive substrate or electrode layer via a bond between a sulfur atom (S) and the conductive substrate or electrode layer). Real time observation of the change in attached amount (molecular density) of the molecule with time (for example, FIG. 2) makes it possible to control the molecular density, the amount of the molecule immobilized or bound on the conductive substrate or electrode layer, to a desired degree. When the electrical potential is controlled based on the indicator of (2) mentioned above, it is not necessary to prepare previously the relation diagram as in the above-mentioned (1).

Figure 3:
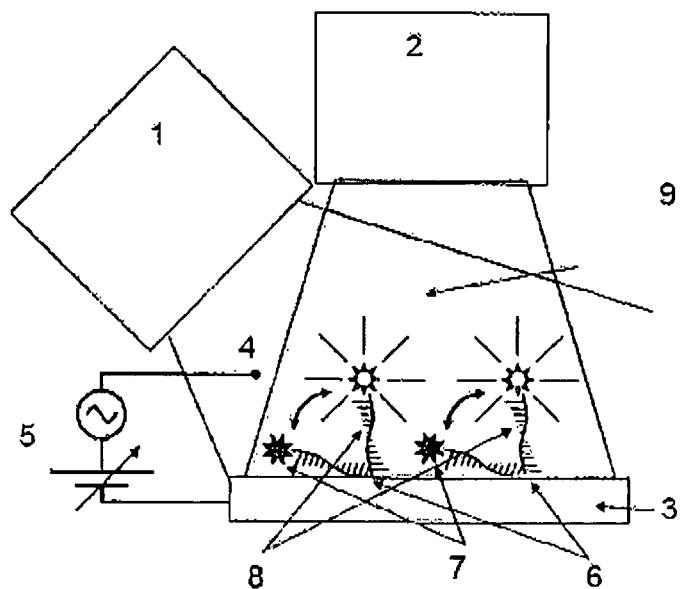
FIG. 3 is a schematic illustration for describing an example of the apparatus, wherein the molecules (DNAs), which comprise a fluorescent dye (fluorescence label) in a molecule thereof, are immobilized or bound on a, gold electrode (the conductive substrate or electrode layer), the molecules are irradiated with light having a wavelength, at which the fluorescent dye can be excited to emit light, by an optical fiber (incident-light fiber), and an optical fiber (light-receiving fiber) that detects the emission by the fluorescent dye (fluorescence label) is provided.

In the case where the electrical potential is controlled based on the indicator of (2) mentioned above, the molecular density of the molecular film is directly monitored, or the signal, which is directly related to the molecular density, is monitored. When the signal, which is directly related to the molecular density, is monitored, it is carried out, for example, as follows. Specifically, when the molecule immobilized or bound on the conductive substrate or electrode layer comprises the fluorescent dye in a molecule thereof as a signal directly related to the molecular density, the fluorescence intensity (a.u.) based on the fluorescent dye is monitored. By such monitoring, the molecular density, the amount of the molecule immobilized or bound on the conductive substrate or electrode layer, can be controlled to a desired degree. Specifically, first, as shown in FIG. 3, the molecule (probe DNA 8) that comprises the fluorescent dye (fluorescence label 7) in a molecule thereof is immobilized or bound on the conductive substrate or electrode layer (gold (Au) electrode 3) through the bond between the sulfur atom (S) and the conductive substrate or electrode layer, i.e., a sulfur atom-gold (S—Au) bond 6 located at the end of the probe DNA 8 to form the molecular film of molecules. When applying the same electrical potential (negative charge) as the charge (negative charge) of the molecule (e.g. DNA) to the conductive substrate or electrode layer (gold electrode 3) and its counter electrode 4 with the power supply 5, the molecule moves away from the conductive substrate or electrode layer due to electrostatic repulsion. Since one end of the molecule is immobilized or bound on the conductive substrate or electrode layer through the S—Au bond, the molecule stays on the conductive substrate or electrode layer as if it stands. When the molecule is irradiated with light having a wavelength at which the fluorescent dye emits fluorescence by an optical fiber, etc., the fluorescent dye emits light differently depending on the position of the molecule, in the case where the molecule is located close to the conductive substrate or electrode layer, emission by the fluorescent dye is weak due to quenching effect, transfer of a part of excitation energy at the time when the fluorescent dye is excited by absorbing light energy of irradiated light to the conductive substrate or electrode layer. On the other hand, in case where the molecule is located apart from the conductive substrate or electrode layer, the quenching effect is diminished, and more excitation energy, generated in the fluorescent dye, is used for emission. As a result, the fluorescent dye emits strong light. Then, this fluorescence is observed at a fluorescence observation area 9 where irradiation light to the molecule by an incident-light fiber 1, and light receiving area of a light-receiving fiber 2 that receives fluorescence from the fluorescence label 7 intersects. This optical detection technique has been described in the literature (see 'Dynamic Electrical Switching of DNA Layers on a Metal Surface' U. Rant et al., Nano Lett., 2004, Vol. 4, No. 12, 2441-2445) and the patent (see 'Analyte evaluating device, and method for evaluating analyte' US patent application, US 2005/0069932 A1).

Figure 4:
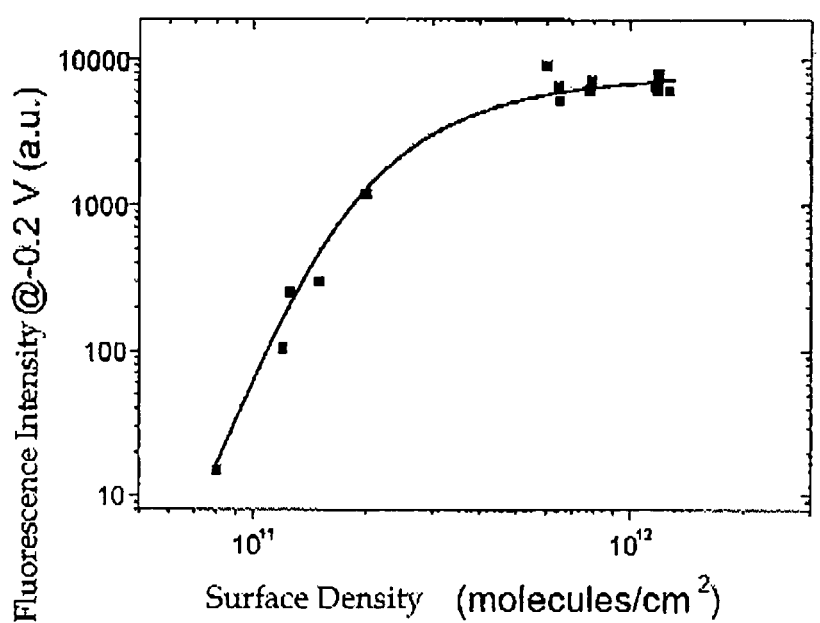
FIG. 4 is a graph showing an experimental value of the relationship between the molecular density (molecules/cm$^2$) of the molecules DNAs) on a gold electrode and the fluorescence intensity (a.u.) generated by the fluorescent dye (fluorescence label) bound to the molecule (DNA), and the molecular density (molecules/cm$^2$) of the molecules (DNAs) on the gold electrode, wherein an electrical potential of −0.2 V is applied to the gold electrode (the conductive substrate or electrode layer), by which the negatively charged molecule (DNA) is extended.

Such fluorescence intensity (a.u.) generated by the fluorescent dye in the molecule is monitored as the signal, and a reduction potential is applied to the conductive substrate or electrode layer. This results in the cleavage of the site of the thiol bond or disulfide bond in the molecule immobilized or bound on the conductive substrate or electrode layer, desorbing the molecules As can be seen in FIG. 4, with the gradual reduction of the density of the molecule (molecules/cm$^2$) on the conductive substrate or electrode layer, the fluorescence intensity (a.u.) is reduced. By stopping application of the reduction potential to the conductive substrate or electrode layer at the time when the fluorescence intensity has exhibited the value corresponding to a desired molecular density, a molecular film with a desired molecular density can be obtained.

—Other Step and Other Unit—

The other step is not particularly limited and can be appropriately selected depending on the application; examples thereof include a supply step described below. The other step can be suitably carried out by the other unit of the apparatus for producing a molecular film with an adjusted density according to the invention, for example, by the supply unit below.

The supply step is a step in which a sulfur atom-containing molecule, smaller than a desorbed molecule, is supplied to the space generated on the conductive substrate or electrode layer upon the desorption of the molecules from the conductive substrate or electrode layer to allow binding of the sulfur atom-containing molecule to the space. The supply step can be suitably carried out by the supply unit of the apparatus for producing a molecular film with an adjusted density.

The supply unit is a unit configured to supply a sulfur atom-containing molecule, smaller than the desorbed molecule, to the space generated on the conductive substrate or electrode layer upon the desorption of the molecules from the conductive substrate or electrode layer to allow binding of the sulfur atom-containing molecule to the space.

In the density adjusting step, when the molecule desorbed from the molecular film is a relatively large molecule such as polymer, typically DNA or protein, diffusion in the solution is slow. Thus, even when the bond between the conductive substrate or electrode layer aid a sulfur atom is cleaved by the reduction, it is highly possible that such molecule stays on the surface of the conductive substrate or electrode layer and readsorbed on these because of slow diffusion from the surface of the conductive substrate or electrode. (See, 'Studies of the Electrochemical Removal and Efficient Re-formation of a Monolayer of Hexadecanethiol Self-Assembled at an Au(111) Single Crystal in Aqueous Solutions' D. F. Yang et al., Langmuir, 1997, Vol. 13, No. 2, 243-249.). In such a case, by protecting the detached portion quickly using molecules with a faster diffusion rate than the desorbed molecule, the readsorption (reattachment) of the desorbed molecule on the conductive substrate or electrode layer is prevented and the desorption of the molecules is facilitated. Thus, it becomes possible to protect the desorbed portion electrically or physically.

The sulfur atom-containing molecule is not particularly limited as long as it comprises at least a sulfur atom, and can be appropriately selected depending on the application. For example, molecules described in 'Characterization of DNA Probes Immobilized on Gold Surfaces' T. M. Herne et al., J. Am. Chem. Soc., 1997, Vol. 119, No. 38, 8916-8920., and 'Quantitative Measurements and Modeling of Kinetics in Nucleic Acid Monolayer Films Using SPR Spectroscopy' R. Georgiadis et al., J. Am. Chem. Soc., 2000, Vol. 122, No. 13, 3166-3173, and the like are suitable. Among these, thiol compounds containing a thiol bond (—SH), disulfide compounds containing a disulfide bond (—S—S—), and the like are suitable, and mercaptohexanol (HO(CH$_2$)$_6$SH: MCH) and the like are most suitable. Since these compounds comprise the thiol bond (—SH) or disulfide bond (—S—S—) in the molecule thereof, they can bind to the conductive substrate or electrode layer easily. In addition, since these compounds have a lower molecular mass than the molecule mentioned above and care excellent in motility (mobility), etc., they bind to the space on the conductive substrate or electrode layer after the desorption of the molecules faster than the desorbed molecule reattaches to the space. Thus, such compounds are advantageous in that readsorption of the desorbed molecule on the conductive substrate or electrode layer can be suitably prevented and in that generation of electrical or physical defect at the space can be prevented effectively. The sulfur atom-containing molecules may be used alone or in combination.

The molecular mass of the sulfur atom-containing molecule is not particularly limited and can be appropriately selected depending on the molecular mass or the like of the molecule. It is preferably smaller than the molecular mass of the molecule, more preferably two times as small as, or smaller than that of the molecule. Specifically, it is preferably three times as small as, or smaller than that of the molecule because it provides better molecular mobility than the molecule.

In the supply step, the sulfur atom-containing molecule can be suitably supplied to the conductive substrate or electrode layer upon or before the cleavage between the molecules and the conductive substrate or electrode layer. Alternatively, the sulfur atom-containing molecule can be suitably supplied to the conductive substrate after the cleavage between the molecules and the conductive substrate or electrode layer.

In the supply step, the amount of the sulfur atom-containing molecule to be supplied to the conductive substrate or electrode layer is not particularly limited and can be appropriately selected depending on the type of the conductive substrate or electrode layer, type or density of the molecule, etc.

—Application of Molecular Film with an Adjusted Density—

The molecular film produced by the method or apparatus for producing a molecular film with an adjusted density according to the invention has an adjusted or reduced molecular density to a desired degree. Thus, the molecular film can be suitably used for a variety of apparatuses or methods for analysis, or measuring devices or measuring methods as a sensor, etc., specifically, as a biosensor such as DNA chip. The molecular film is formed on the conductive substrate or electrode layer, and those comprising the molecular film on the conductive substrate or electrode layer can be used, for example, as a device such as biosensor. Thus, the apparatus for producing a molecular film with an adjusted density according to the invention can be employed as a device, analyzer, measuring device, etc, including biosensor without further processing after the formation of the molecular film.

The molecular film with an adjusted density produced according to the invention can be used as follows, for example. Specifically, applying an electrical potential to the conductive substrate or electrode layer on which the molecular film is formed, or varying the applied electrical potential can desorb the molecules adsorbed on the conductive substrate or electrode layer from the conductive substrate or electrode layer. For example, varying the electrical potential of the conductive substrate or electrode layer to which a positive electrical potential is applied, to a negative electrical potential, or varying the electrical potential of the conductive substrate or electrode layer to which a reduction potential (negative electrical potential) is applied, to a positive electrical potential allows for the desorption of the molecules. For example, when the molecule is a polynucleotide (DNA) that comprises the thiol bond (—SH) or disulfide bond (—S—S—) at its end, the polynucleotide is bound to the conductive substrate or electrode layer via the sulfur atom (S) of the thiol bond or disulfide bond. Since the polynucleotide itself is negatively charged, application of a positive electrical potential to the conductive substrate or electrode layer causes the polynucleotide molecules to be attracted to the conductive substrate or electrode layer due to electrostatic attraction In contrast when a negative electrical potential is applied to the conductive substrate or electrode layer, the polynucleotide molecules move around the bond between the sulfur atom (S) and the conductive substrate or electrode layer and stay away from the conductive substrate or electrode layer due to electrostatic repulsion to the conductive substrate or electrode layer. Thus, application of a desired electrical potential to the molecular film as described above enables to attract each molecule making up the molecular film on the conductive substrate or electrode layer or to move each molecule away from it, thereby making a desired control possible depending on the type, purpose, etc. of analysis or measurement.

When analysis, measurement, or the like is performed employing the molecular film produced by the method or apparatus for producing a molecular film with an adjusted density according to the invention, the molecular film is typically used by immersing in an aqueous solution.

The aqueous solution is not particularly limited as long as it is solution, and can be appropriately selected depending on the application; examples thereof include water, electrolyte, and buffered saline. These may be used alone or in combination.

When performing analysis, measurement, or the like employing the molecular film, solutions of a nonaqueous electrolyte may be used instead of the aqueous solution, by which water-insoluble substances can be analyzed or measured. In this case, examples of suitable nonaqueous electrolyte include organic solvents; specifically, acetonitrile, benzonitrile, and tetrahydrofuran are suitable, for example.

Examples of the invention are illustrated below, but these are not to be construed as limiting the invention.

EXAMPLES

—Molecular Film Forming Step (Unit)—

Using as the molecule a single stranded DNA that has a thiol group at one end and a fluorescent cyanine dye (Cy3) as the fluorescent dye (fluorescence label) at the other end (24 base probe DNA: ss-24mer-probe-DNA), a molecular film (dense film) was formed by self-assembly of the DNAs as follows. Specifically, according to the method described in 'Formation and Structure of Self-Assembled Monolayers' A. Ulman, Chem. Rev., 1996, Vol. 96, No. 4, 1533-1554, the DNAs were immobilized or bound on a gold electrode (2 mm $\phi$) as the conductive substrate or electrode layer via a sulfur atom to form a molecular film (dense film) of the DNAs on the gold electrode.

Next, in order to perform the density adjusting step by adjusting (reducing) the molecular density of the DNA making up the molecular film using a fluorescence intensity generated by the fluorescent dye (fluorescence label) as an indicator, as shown in FIG. 3, can incident-light fiber 1 and a light-receiving fiber 2 were arranged so that an electrical (reduction potential) potential can be applied to the gold electrode 3 and its counter electrode 4 by the power supply 5 through a lead line. The incident-light fiber 1 illuminates DNAs (probe DNAs) 8 immobilized or bound on the gold electrode 3, and the light-receiving fiber 2 receives the fluorescence from the fluorescence label 7 of the DNAs 8.

—Density Adjusting Step (Unit)—

When applying an electrical potential of –0.2 V relative to the counter electrode 4 with the power supply 5 so that a negative electric potential, the same polarity as the charge of DNA 8 (negative charge), is applied to the gold electrode 3, the DNA 8 is located apart from the gold electrode 3 due to the electrostatic repulsion to the gold electrode 3. Since one end of the DNA 8 is immobilized or bound on the gold electrode 3 through a thiol bond 6, the DNA 8 stays on the gold electrode 3 as if it stands. Then, the DNA 8 is irradiated with light having a wavelength at which the fluorescent dye emits fluorescence upon absorption by the incident-light fiber 1. In the case where the DNA 8 is located close to the gold electrode 3, emission by the fluorescent dye is reduced or does not occur due to quenching effect, transfer of a part of excitation energy at the time when the fluorescence label 7 is excited by absorbing light energy of irradiated light, to the gold electrode in the case where the DNA 8 is located apart from the gold electrode 3, the quenching effect is diminished, and more excitation energy generated in the fluorescence label 7, is used for emission. As a result, emission by the fluorescence label 7 is increased. Then, this fluorescence is observed at the fluorescence observation area 9 where irradiation light to the DNA 8 by the incident-light fiber 1, and light-receiving area of the light-receiving fiber 2 that receives fluorescence from the fluorescence label 7 of the DNA 8 intersects.

When a relatively large reduction potential of –0.6 V to –0.8 V is further applied to the gold electrode 3, the thiol bond 6 of the DNA 8 is cleaved by the reduction potential, resulting in the decrease of the molecular density (molecules/cm$^2$). Initially, the molecular density of the DNAs 8 was about $1.2 \times 10^{12}$ (molecules/cm$^2$). By the reductive desorption due to the application of the reduction potential, DNAs 8 were gradually desorbed from the gold electrode 3, resulting in a reduced molecular density of about $8 \times 10^{10}$ (molecules/cm$^2$). The relationship between the fluorescence intensity (a.u.) generated by the fluorescence label 7, and the molecular density (molecules/cm$^2$) of the DNAs 8 on the gold electrode 3 was measured, which is shown in the graph of FIG. 4. During the measurement of fluorescence intensity, a negative electrical potential of −0.2 V was applied, the DNA 8 was made stood, and the distance between the gold electrode 3 and fluorescence label 7 was maintained constant. The reason for this is to prevent the change of fluorescence intensity due to quenching effect. Specifically, since a part of excitation energy is transferred to the electrode (quenching effect), change of the distance between the fluorescence label 7 and gold electrode 3 results in the change of fluorescence intensity.

Figure 5:
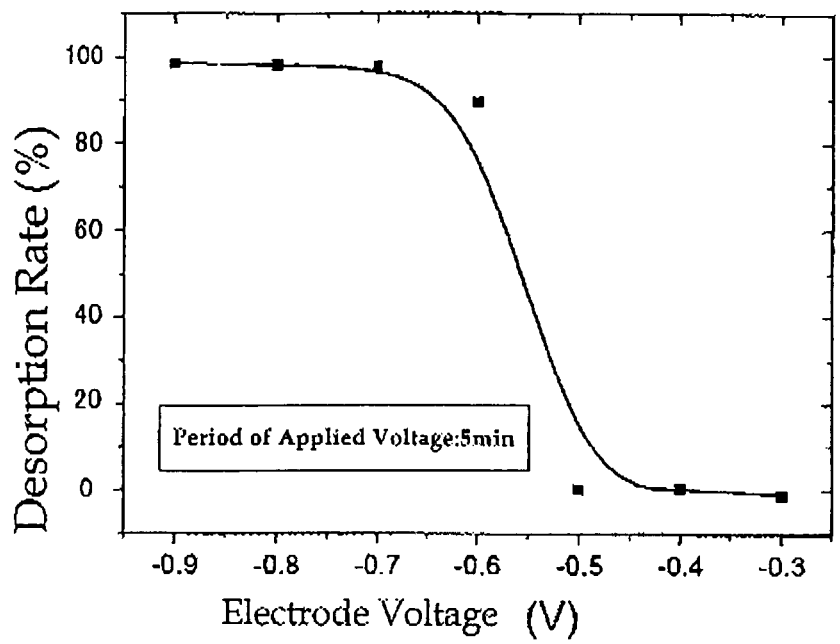
FIG. 5 is a graph showing a desorption rate (%) of the molecule (DNA) in the case where the molecules (DNAs) immobilized or bound on a gold electrode (the conductive substrate or electrode layer) via a sulfur atom (S) are desorbed by applying a reduction potential to the gold electrode.

Next, a plurality electrodes having molecular films of DNAs 8 with an initial molecular density of about $1 \times 10^{12}$ (molecules/cm$^2$) was prepared and different electrical potentials of from −0.3 V to −0.9 V were applied, and the desorption rate of DNA 8 at each electrical potential was measured. As shown in FIG. 5, a large change (0% to 100%) in desorption rate (%) of DNA 8 was observed between −0.4 V and −0.7 V.

From the results of FIG. 5, it was found that a desorpttion rate of 80% was obtained at −0.6 V. Thus, by applying a reduction potential of −0.6 V to the gold electrode 3, the DNAs 8 were desorbed gradually from the gold electrode 3 as shown in FIG. 6, and the molecular density of DNAs 8 was reduced (adjusted) from initial $1 \times 10^{12}$ (molecules/cm$^2$) to $2 \times 10^{11}$ (molecules/cm$^2$).

Figure 6:
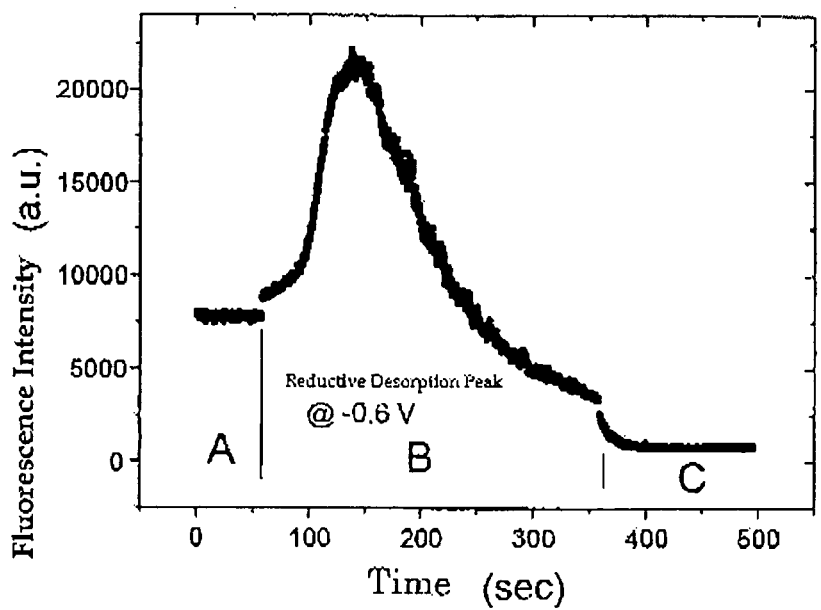
FIG. 6 is a graph showing a result of the experiment where the molecular density of the molecular film of DNAs with an initial molecular density of $1 \times 10^{12}$ cm$^{-2}$ was reduced to $2 \times 10^{11}$ cm$^{-2}$.

In the graph shown in FIG. 6, initial time period (0 to about 60 seconds), the following time periods (about 60 seconds to about 360 seconds) and (about 360 seconds to about 500 seconds) are designated as "A", "B", and "C", respectively. The fluorescence intensity (a.u.) in "A" is due to the fluorescence label 7 of the DNAs 8 (molecular film) with an initial molecular density. The fluorescence intensity (a.u.) in "C" is due to the fluorescence label 7 of the DNAs 8 with a decreased molecular density after the desorption of DNAs 8 by the application of a reduction potential to the gold electrode 3. The fluorescence in "B" is due to the fluorescence label 7 of the DNAs 8 immediately after the desorption from the gold electrode 3 upon application of a reduction potential to the gold electrode 3. Since the quenching effect is eliminated completely, large fluorescence was observed temporarily. From the results of FIG. 5, the molecular density after the desorption form the gold electrode 3 by the application of a reduction potential (negative electrical potential) of −0.6 V to the gold electrode 3 for 5 minutes, that is, the molecular density giving the fluorescence intensity in "C" of the graph of FIG. 6 was calculated as $2 \times 10$ cm$^2$. It was confirmed that this value is well consistent with the experimental value using the electrochemical method as described in 'Electrochemical Quantization of DNA Immobilized on Gold' A. B. Steel et al., Anal. Chem., 1998, Vol. 70, No. 22, 4670-4677.

By the density adjusting step described above, the molecular density of the molecular film of DNAs 8 with a relatively dense molecular density was adjusted (reduced) to a desired degree easily.

Figure 7:
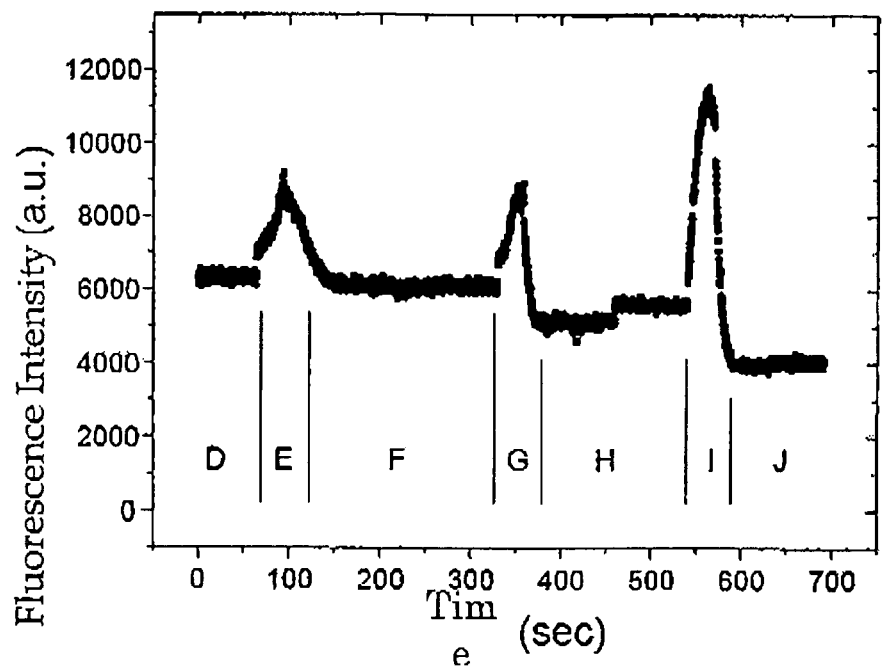
FIG. 7 is a graph showing that while monitoring fluorescence by a fluorescent dye of a molecule that comprises the fluorescent dye (fluorescence label), an electrical potential (reduction potential) of −0.6 V are applied to a gold electrode (the conductive substrate or electrode layer) three times, and the molecular density of the molecular film of the molecules immobilized or bound on the gold electrode is stepwise reduced.

Next, while monitoring fluorescence by the fluorescence label 7 of the DNA 8 in real time, a reduction potential (negative electrical potential) of −0.6 V was applied to the gold electrode 3 three times, each for 30 seconds, by which the molecular density of the molecular film of DNAs 8 immobilized or bound on the gold electrode 3 was stepwise decreased (adjusted). The results are show in FIG. 7, In FIG. 7, initial time period (0 to about 70 seconds), the following time periods (about 70 seconds to about 120 seconds), (about 120 seconds to about 330 seconds), (about 330 seconds to about 370 seconds), (about 370 seconds to about 540 seconds), (about 540 seconds to about 580 seconds), and (about 580 seconds to about 700 seconds), are designated as "D", "E", "F", "G", "H", "I", and "J", respectively. Starting from the fluorescence intensity (a.u.) in "D" corresponding to the initial molecular density, by the gradual desorption of DNAs 8 from the gold electrode 3, the fluorescence intensity (a.u.) reached the fluorescence intensity (a.u.) in "J" corresponding to the final molecular density through "F" and "H". Each peak of "E", "G", and "I" means temporary fluorescence from desorbing DNAs 8. From the graph of FIG. 4 showing a relationship between fluorescence intensity (a.u.) and surface density (molecular density), the molecular density giving the fluorescence intensity in "J" corresponding to the final molecular density was estimated as $4 \times 10^{11}$ cm$^{-2}$. It was confirmed that this value is well consistent with the experimental value using the electrochemical method mentioned above.

—Supply Step (Unit)—

Figure 8:
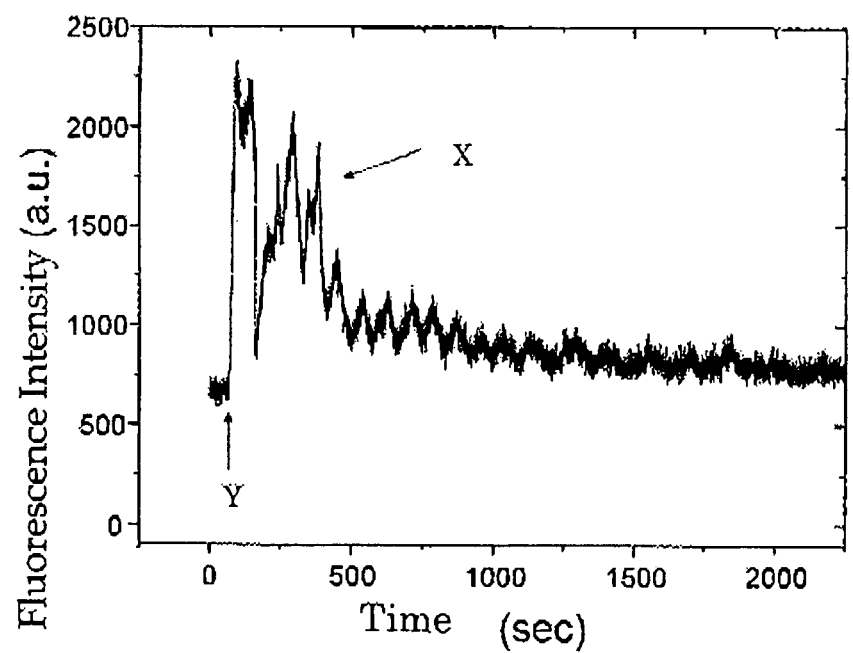
FIG. 8 is a graph showing a result of the experiment where using the invention, the desorption of DNA, whose bond with a gold electrode was cleaved by reduction, was facilitated by the addition of MCH.

Next, DNAs 8 were desorbed from the gold electrode 3 from an initial molecular density of $2.2 \times 10^{11}$ cm$^{-2}$ until a final molecular density of $1.5 \times 10^{11}$ cm$^{-2}$. During the desorption, mercaptohexanol (HO(CH$_2$)$_6$SH: MCH) as the sulfur atom-containing molecule, winch is a molecule smaller than the DNA 8, was supplied to the space on the gold electrode 3 from which the DNAs 8 desorbed, allowing the binding of the MCH to the space. As a result, as shown in FIG. 8, immediately after the addition of the MCH ("Y" in FIG. 8), fluorescence peak due to the desorption of DNAs 8 was observed ("X" in FIG. 8: signal due to the desorption of DNAs witch was facilitated by the addition of the MCH). It was also confirmed that the effect of facilitating desorption by a relatively small thiol molecule (the MCH) is effective when the DNAs 8 re desorbed from the gold electrode 3 by applying an electrical potential for desorption repeatedly.

The present invention can solve conventional, problems and can provide a technique that can adjust the molecular density of the film of functional molecules (e.g. DNA molecules), which is utilized for biochips such as DNA chip, to a desired degree efficiently and easily, in other words, can provide a method and apparatus for producing a molecular film with an adjusted density that is suitable for biochips such as DNA chip.

By the method or apparatus for producing a molecular film with an adjusted density according to the invention, a molecular film, whose molecular density is adjusted (reduced) to a desired degree, can be obtained, and in the resulting molecular film, motility of each molecule making up the molecular film, and the like are not inhibited and are favorable. Thus, the molecular film can be suitably used for a variety of diagnoses, analyses, measurements, detection, and the like for e.g. various diseases, When the molecule comprises the target capture portion, diagnosis, analysis, measurement, detection, etc, of various useful molecules such as protein can be also performed, and in addition, by providing the light-emitting portion, even quantification of the useful molecule can be performed.

The method or apparatus for producing a molecular film with an adjusted density according to the invention is extremely useful in the field of nanobiotechnology, and the molecular film, obtained by the invention and having a molecular density adjusted to a desired degree, is remarkably contributes to the improvement of performance, reliability, quantitative ability, and reproducibility of device, etc.

What is claimed is:

1. A method for producing a molecular film with an adjusted density, comprising:
   forming a molecular film composed of molecules on a conductive substrate,
   wherein the molecule comprises a region capable of binding to the conductive substrate at least in a portion thereof, and the molecular film is a dense molecular film formed by self-assembly; and adjusting a molecular density of the molecular film by desorbing a part of the molecules which make up the molecular film from the conductive substrate.

2. The method for producing a molecular film with an adjusted density according to claim 1, wherein the adjusting the molecular density is performed by applying an electrical potential to the conductive substrate to desorb molecules and to thereby reduce the molecular density of the molecular film.

3. The method for producing a molecular film with an adjusted density according to claim 1, wherein the adjusting a molecular density is performed such that a relation diagram between desorption rate (%) and applied voltage (V) is prepared in advance, and while adjusting the magnitude of electrical potential to be applied to the conductive substrate and applied period based on the relation diagram, an electrical potential is applied to the conductive substrate to desorb molecules and to thereby reduce the molecular density of the molecular film, wherein the desorption rate (%) means an amount of desorbed molecule per unit time during the application of the electrical potential.

4. The method for producing a molecular film with an adjusted density according to claim 1, wherein the adjusting a molecular density is performed such that while monitoring the molecular density on the conductive substrate in real time, or while monitoring a signal directly related to the molecular density on the conductive substrate in real time, an electrical potential is applied to the conductive substrate to desorb molecules and to thereby reduce the molecular density of the molecular film.

5. The method for producing a molecular film with an adjusted density according to claim 4, wherein the molecule comprises a fluorescent dye in a molecule thereof, and the signal directly related to the molecular density on the conductive substrate is a fluorescence intensity generated by the fluorescent dye.

6. The method for producing a molecular film with an adjusted density according to claim 1, wherein the molecule comprises a sulfur atom in a portion thereof and is capable of binding to the conductive substrate via the sulfur atom.

7. The method for producing a molecular film with an adjusted density according to claim 1, wherein the electrical potential is reduction potential.

8. The method for producing a molecular film with an adjusted density according to claim 1, further comprising supplying a sulfur atom-containing molecule which is smaller than the desorbed molecule, to a space generated on the conductive substrate upon the desorption of the molecules from the conductive substrate to allow binding of the sulfur atom-containing molecule to the space.

9. The method for producing a molecular film with an adjusted density according to claim 8, wherein in the supplying, the sulfur atom-containing molecule is supplied to the conductive substrate upon or before the desorption of the molecules from the conductive substrate.

10. The method for producing a molecular film with an adjusted density according to claim 8, wherein in the supplying, the sulfur atom-containing molecule is supplied to the conductive substrate after applying an electrical potential for the desorption of the molecules from the conductive substrate.

* * * * *